United States Patent [19]

Beck et al.

[11] 4,304,783
[45] Dec. 8, 1981

[54] THIENYL, THIENYLOXY OR FURYL SUBSTITUTED PROSTAGLANDIN DERIVATIVES IN THE 6-KETO-PGE$_1$ SERIES

[75] Inventors: Gerhard Beck, Frankfurt am Main; Ulrich Lerch, Hofheim am Taunus; Bernward Schölkens, Kelkheim; Richard H. Rupp, Frankfurt am Main, all of Fed. Rep. of Germany

[73] Assignee: Hoechst Aktiengesellschaft, Frankfurt am Main, Fed. Rep. of Germany

[21] Appl. No.: 136,819

[22] Filed: Apr. 3, 1980

[30] Foreign Application Priority Data

Apr. 6, 1979 [DE] Fed. Rep. of Germany ....... 2913856

[51] Int. Cl.$^3$ ................. A61K 31/557; C07D 307/54; C07D 333/24
[52] U.S. Cl. .................................... 424/275; 424/285; 549/66; 549/79; 260/347.3; 260/347.4
[58] Field of Search ........................ 560/53, 118, 121; 562/463, 500, 503; 549/66, 79; 260/347.3, 347.4; 424/275, 285, 305, 308, 317

[56] References Cited

U.S. PATENT DOCUMENTS 4,205,178  5/1980  Axen ................................... 562/503
4,215,142  7/1980  Hayashi et al. ..................... 562/503

Primary Examiner—Henry R. Jiles
Assistant Examiner—Bernard Dentz
Attorney, Agent, or Firm—Curtis, Morris & Safford

[57] ABSTRACT

The invention relates to new prostaglandin derivatives of the 6-keto-PGE$_1$ series, to processes and intermediates for their manufacture and to their use as medicaments.

5 Claims, No Drawings

THIENYL, THIENYLOXY OR FURYL SUBSTITUTED PROSTAGLANDIN DERIVATIVES IN THE 6-KETO-PGE$_1$ SERIES

Prostaglandins are a group of fatty acids which are found in numerous tissues and organs of humans and animals. The skeleton of the naturally occurring prostaglandins consists of 20 carbon atoms which are arranged in the form of a five-membered ring and two adjacent linear side chains.

The pharmacological effects of the prostaglandins extend, inter alia, into the fields of reproduction, the bronchial muscle tone, the blood pressure and gastroenterology. The pharmacological characteristics of the naturally occurring prostaglandins are the subject of numerous review articles, for example by N. H. Andersen and P. W. Ramwell in Arch. Internal Med. 133, 30 (1974); R. L. Jones in Pathobiology Ann. 1972, 359; J. Pike in Scient. American 225, 84 (1971) or M. P. L. Caton in Progress in Med. Chem. Volume 7, ed.: Butterworth, London 1971.

The synthesis of analogs of prostanoic acids, which are not naturally occurring and in which the large number of pharmacological effects of the naturally occurring prostaglandins are differentiated, is becoming increasingly important.

The present invention relates to new compounds of the formula I

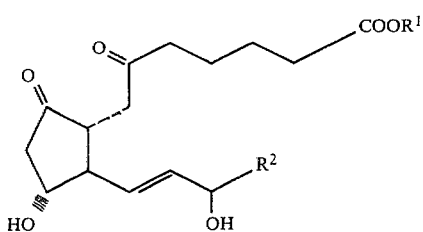

which are structurally related to the naturally occurring prostaglandins and in which $R^1$ denotes hydrogen or a straight-chain or branched alkyl radical with up to 6 carbon atoms or a straight-chain or branched unsaturated aliphatic hydrocarbon radical with up to 6 carbon atoms or a cycloaliphatic hydrocarbon radical with 3 to 7 carbon atoms or an araliphatic hydrocarbon radical with 7 to 9 carbon atoms or a physiologically acceptable metal ion, NH$_4$ ion or ammonium ion derived from a primary, secondary or tertiary amine, or a tetraalkylammonium ion and $R^2$ denotes (a) a cycloalkyl radical with 3 to 7 carbon atoms or (b) a straight-chain or branched alkyl radical with up to 8 carbon atoms, in which a CH$_2$ group which is not a terminal group can be replaced by an oxygen atom, or which alkyl radical can be substituted (b$_1$) by halogen or by an α- or β-thienyl or-furyl radical, which, in turn, can be monosubstituted to trisubstituted in the nucleus by halogen, trifluoromethyl and/or alkyl or alkoxy, each with 1–6 C atoms, or (b$_2$) by a phenoxy radical, an α-or β-thienyloxy radical or a cycloalkoxy radical with 3 to 7 carbon atoms, it being possible for the said radicals, in turn, to be monosubstituted to trisubstituted in the nucleus by halogen, trifluoromethyl and/or alkyl or alkoxy, each with 1–6 C atoms.

Amongst the substituents mentioned for $R^1$, the following are preferred: hydrogen, a straight-chain or branched alkyl radical with up to 8 C atoms, a straight-chain or branched unsaturated aliphatic hydrocarbon radical with up to 4 C atoms, a cycloaliphatic hydrocarbon radical with 5–7 C atoms and an araliphatic hydrocarbon radical with 7 to 8 C atoms.

Particularly preferred substituents are: hydrogen, methyl, ethyl, n-butyl, n-pentyl, n-hexyl, n-heptyl, 2-propyl, 2-butyl, 2-pentyl, 3-hexyl, 2-methylpropyl, 2-methylbutyl, 4,4-dimethylpentyl, 5,5-dimethylhexyl, cyclopentyl, cyclohexyl and cycloheptyl.

Amongst the substituents mentioned for $R^2$, the following are preferred: cycloalkyl with 5 to 7 C atoms, straight-chain alkyl radicals with 3 to 7 C atoms, branched alkyl radicals with up to 8 C atoms, in which a CH$_2$ group which is not a terminal group can be replaced by an oxygen atom, and straight-chain or branched alkyl radicals with up to 5 C atoms, which are substituted by halogen, thienyl, furyl, chlorothienyl, phenoxy, chlorophenoxy, thienyloxy, chlorothienyloxy or cyclohexyloxy.

Particularly preferred substituents are: 1,1-dimethyl-2-butoxy-ethyl, 1,1-dimethyl-pentyl, n-propyl, 2-propyl, n-butyl, 2-butyl, t-butyl, n-pentyl, 3-pentyl, 2-methylbutyl, neopentyl, n-hexyl, 2-ethylbutyl, 2,2-dimethylbutyl, n-heptyl, 1,1-dimethyl-2-ethoxy-ethyl, 1,1-dimethyl-2-methoxy-ethyl, 1,1-dimethyl-cyclohexyloxymethyl, 1-fluoropentyl, 1-chloropentyl, 5-fluoropentyl, 5-chloropentyl, 3-thienyl-2-ethyl, 2-thienyl-2-ethyl, 3-(2-chloro-thienyl)-2-ethyl, 2-(5-chloro-thienyl)-2-ethyl, phenoxymethyl, 3-chloro-phenoxymethyl, 2-thienyl-oxymethyl, 3-(2-chlorothienyl)-oxymethyl, 2-(5-chlorothienyl)-oxymethyl, 3-furyl-2-ethyl, 2-furyl-2-ethyl, cyclopentyl, cyclohexyl and cycloheptyl.

The invention also relates to a process for the manufacture of compounds of the formula I, which comprises (a) eliminating HX, with the aid of a base, from a compound of the formula II

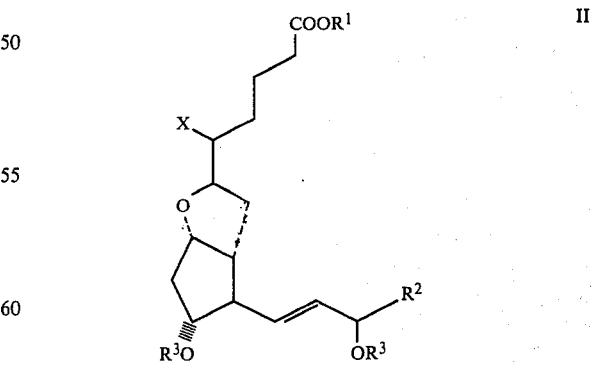

in which $R^1$ and $R^2$ have the meaning indicated under formula I, $R^3$ denotes an easily detachable protective group and X denotes a halogen atom, a compound of the formula III

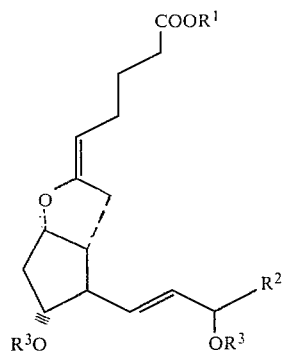

being obtained, in which $R^1$ and $R^2$ have the meaning indicated under formula I and $R^3$ denotes an easily detachable protective group, (b) subjecting a compound of the formula III to acid hydrolysis to give a compound of the formula IV

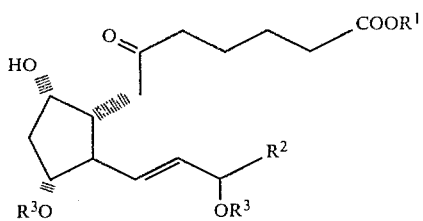

in which $R^1$ and $R^2$ have the meaning indicated under formula I and $R^3$ denotes an easily detachable protective group, (c) converting a compound of the formula IV by oxidation to a compound of the formula V

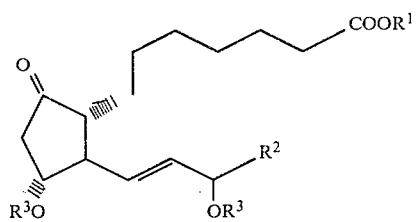

in which $R^1$ and $R^2$ have the meaning indicated under formula I and $R^3$ denotes an easily detachable protective group, (d) detaching the protective groups $R^3$ from a compound of the formula V under suitable neutral or acid conditions, a compound of the formula I in which $R^1$ and $R^2$ have the meaning indicated under formula I being formed, and (e) if desired, converting a compound of the formula I in which $R^1$ does not represent hydrogen or a cation by acid or alkaline hydrolysis to a compound of the formula I in which $R^1$ denotes hydrogen or a physiologically acceptable cation; and (f) if desired, in a compound of the formula I in which $R^1$ denotes a physiologically acceptable metal ion, $NH_4$ ion or ammonium ion, derived from a primary, secondary or tertiary amine, or a tetraalkylammonium ion, replacing the cation $R^1$ by another cation.

The procedures used to manufacture the prostaglandin derivatives of the formula II used as the starting material in the process according to the invention can be analogous to the processes which are described, for example, in German Offenlegungsschrift No. 2,811,950.

The elimination of HX, where X preferably denotes bromine or iodine, from compounds of the formula II with the formation of compounds of the formula III proceeds under the action of bases in the presence or absence of a solvent.

Bases which can be used are both inorganic and organic bases, such as, for example, alkali metal hydroxides or alkali metal carbonates, alcoholates, such as, for example, sodium methylate or potassium tertiary butylate, amines, such as, for example, triethylamine, 4-dimethylaminopyridine, dicyclohexylethylamine or 1,4-diazabicyclo[2.2.2]octane, or amidines, such as, for example, 1,5-diazabicyclo[3.4.0]non-5-ene (DEN) or 1,5-diazabicyclo[5.4.0]undec-5-ene (DBU). The hydrolysis of compounds of the formula III to compounds of the formula IV is carried out by acid catalysis at temperatures between $-10°$ C. and $+20°$ C., appropriately in an alcoholic or aqueous organic solvent. Suitable acids are dilute mineral acids or organic acids such as p-toluene-sulfonic acid, oxalic acid or acetic acid.

The compounds of the formula IV are converted to compounds of the formula V by oxidation. Suitable oxidizing agents are, in particular, chromic acid, chromic acid/pyridine complexes, Jones reagent and pyridinium chlorochromate. Suitable solvents are those which cannot be oxidized themselves, such as, for example, acetone, ether and methyl chloride.

The compounds of the formula V in which $-COOR^1$ represents an ester group are converted to compounds of the formula I in which $-COOR^1$ represents an ester group by removing the protective groups $R^3$ in the presence of dilute mineral acid or organic acids such as p-toluene-sulfonic acid, oxalic acid or acetic acid, appropriately in an aqueous/organic solvent, such as, for example, tetrahydrofuran/water.

Compounds of the formula I in which $R^1$ denotes an alkyl radical can be saponified in a conventional manner in an alkaline medium to give compounds of the formula I in which $R^1$ denotes hydrogen or preferably a cation, for example using NaOH or KOH in a low-molecular alcohol, such as methanol, or ether, such as dimethoxyethane or THF, optionally in the presence of water. Advantageously, the equimolar amount or a very slight excess of alkali metal hydroxide is used, so that the alkali metal salt of the formula I ($R^1$=alkali metal ion) is obtained by evaporating the solvent.

The alkali metal cation can be replaced by any desired cations on ion exchangers in a conventional manner. For this purpose, the solution of the alkali metal salt of a compound of the formula I is allowed to run through a column filled with a cation exchanger, such as, for example, ®Amberlite CG - 50 or ®Dowex CCR - 2.

The cation exchanger is charged with the desired cation, for example with an ammonium ion which is derived from a primary, secondary or tertiary amine. The desired salt is obtained by evaporating the eluate. The compounds of the formula II, III, IV and V can be employed for the subsequent reactions in the form of a mixture of diastereomers with respect to the position of the hydroxyl group on carbon atom 15 (prostaglandin nomenclature), in the form of pure $\alpha$- or $\beta$-isomers or in the form of optically active antipodes. The separation of stereoisomers or the resolution of antipodes can, however, also be effected after any subsequent reaction stage. This means that all the reactions described can be carried out with mixtures of diastereomers, with pure diastereomers or with optically active antipodes.

If the individual reaction products are not obtained in a form which is already sufficiently pure for them to be employed for the subsequent reaction step, purification by means of, for example, column chromatography, thin layer chromatography or high-pressure liquid chromatography is advisable.

In addition to the compounds named in the examples, the following compounds in particular can also be manufactured by the processes according to the invention: 16-chloro-6-keto-PGE$_1$ methyl ester, 16-chloro-6-keto-PGE$_1$, 16-fluoro-6-keto-PGE$_1$ ethyl ester, 17-(2-thienyl)-18, 19, 20-trinor-6-keto-PGE$_1$, 17-(3-(2-chlorothienyl)-18, 19, 20-trinor-6-keto-PGE$_1$ methyl ester, 16-phenoxy-17, 18, 19, 20-tetranor-6-keto-PGE$_1$ ethyl ester, 16-(3-trifluoromethyl-phenoxy)-17, 18, 19, 20-tetranor-6-keto-PGE$_1$ n-butyl ester, 16-(3-(2-chloro)-thienyloxy)-17, 18, 19, 20-tetranor-6-keto-PGE$_1$ methyl ester, 16-(2-thienyloxy)-17, 18, 19, 20-tetranor-6-keto-PGE$_1$ methyl ester, 17-(3-furyl)-18, 19, 20-trinor-6-keto-PGE$_1$, 15-cyclopentyl-16, 17, 18, 19, 20-pentanor-6-keto-PGE$_1$ propyl ester, 15-cyclopentyl-16, 17, 18, 19, 20-pentanor-6-keto-PGE$_1$, 17-oxa-6-keto-PGE$_1$ methyl ester, 16, 16-dimethyl-17-oxa-21-homo-6-keto-PGE$_1$, 17-oxa-16, 16, 19-trimethyl-6-keto-PGE$_1$ n-butyl ester, 16, 16-dimethyl-18-oxa-21-homo-6-keto-PGE$_1$, 19-oxa-6-keto-PGE$_1$ ethyl ester, 16, 16-diethyl-19-oxa-6-keto-PGE$_1$ methyl ester, 19-oxa-16, 16, 20, 20-tetramethyl-6-keto-PGE$_1$ isopropyl ester, 18, 18-dimethyl-19-oxa-6-keto-PGE$_1$ and 16, 16-dimethyl-20-oxa-21-homo-6-keto-PGE$_1$ methyl ester.

The compounds of the formula I are distinguished by an inhibitory action on thrombocyte aggregation, relaxation of the vascular wall, especially of the coronary arteries, and hypotensive properties.

They can therefore be used as medicaments. The compounds of the formula I are used as hypotensive agents in a daily dosage range of 0.001 mg–0.1 mg/kg and preferably 0.005 mg–0.1 mg/kg in the case of intravenous administration and in a daily dosage range of 0.001 mg–1 mg/kg and preferably 0.05–1 mg/kg in the case of oral administration. Proper unit dosages amount to about one third of the mentioned daily dosages. For relaxation of the vascular wal, especially of the coronary arteries, and for inhibition of thrombocyte aggregation, dosages lower than those indicated above are also effective in some cases.

The compounds, according to the invention, of the formula I can be used in the form of the free acids or in the form of their physiologically acceptable inorganic or organic salts or in the form of esters. Acids and salts or esters can be used in the form of their aqueous solutions or suspensions or also as solutions or suspensions in pharmacologically acceptable organic solvents, such as monohydric or polyhydric alcohols, such as, for example, ethanol, ethylene glycol or glycerol, oils, such as, for example, sunflower oil or cod-liver oil, ethers, such as, for example, diethylene glycol dimethyl ether, or also polyethers, such as, for example, polyethylene glycol, or in the presence of other pharmacologically acceptable polymeric carriers, such as, for example, polyvinylpyrrolidone.

Formulations which can be used are the customary galenical infusion or injection solutions and tablets, and also formulations for local application, such as creams, emulsions, suppositories or aerosols.

A further use of the new compounds lies in the combination with other active compounds. In addition to other suitable substances, these include, in particular: circulatory preparations in the broadest sense, such as, for example, cardiac glycosides, such as digitoxin, sympathomimetic agents, such as Suprifen, β-sympatholytic agents, such as Inderal, coronary dilators, such as chromonar or prenylamine, hypotensive substances, such as reserpine or clonidine, antiarrhythmic agents, substances which stimulate the blood flow, anticoagulants or fibrinolytic agents, diuretic agents, such as, for example, furosemide, substances which lower the lipid level, prostaglandins or prostaglandin antagonists or prostaglandin biosynthesis inhibitors, such as, for example, non-steroid antiphlogistic agents, thromboxane synthetase inhibitors, psychopharmaceuticals and vitamins.

The compounds of the formula II, III, IV and V are new, valuable intermediates for the manufacture of compounds of the formula I.

EXAMPLE 1

(a)

5-Iodo-16-(3-thienyloxy)-11,15-bis-tetrahydropyranyloxy-17,18,19,20-tetranor-PGI$_1$ methyl ester

II 450 mg (0.84 mmole) of 5-iodo-16-(3-thienyloxy)-17,18,19,20-tetranor-PGI$_1$ methyl ester (prepared analogously to DE-OS No. 2,811,950) are dissolved in 6 ml of absolute methylene chloride.

84×5=420 mg (5 mmoles) of distilled dihydropyran and also a small spatula tip (about 5 mg) of p-toluenesulfonic acid are then added and the reaction mixture is stirred for 1 hour at room temperature. After the reaction has ended, the methylene chloride phase is washed with saturated NaHCO$_3$ solution until acid-free, dried over magnesium sulfate and filtered and the filtrate is concentrated to dryness in vacuo.

Yield: 0.57 g of a pale yellow oil (II).

TLC$_{in\ ethyl\ acetate}$ Rf=0.9.

Staining with molybdophosphoric acid.

Plate warmed to 100° C.

| NMR: δ values in CDCl$_3$ | 1.0–2.8 | (m, 24H) | —CH$_2$—, CH— |
|---|---|---|---|
| | 3.6 | (s, 3H) | OCH$_3$ |
| | 3.9 | (d, 2H) | —CH$_2$—O—thiophen |
| | 4.5–4.7 | (m, 3H) | —CHI—, —O—CH—O— |
| | 5.3–5.7 | (m, 2H) | olefinic proton |
| | 6.15–7.3 | (m, 3H) | thiophen |

EXAMPLE 1 b

5-Iodo-17-(3-thienyl)-11,15-bis-tetrahydropyranyloxy-18,19,20-trinor-PGI$_1$ methyl ester Obtained from 5-iodo-17-(3-thienyl)-18,19,20-trinor-PGI$_1$ methyl ester by reaction analogous to Example 1 a.

| NMR (CDCl$_3$) δ values: | 1.1–2.9 | (m, 26H) | —CH$_2$—, >CH— |
|---|---|---|---|
| | 3.6 | (s, 3H) | OCH$_3$ |
| | 4.6–4.8 | (m, 3H) | —O—CH—O—, —CH—I |
| | 3.5–4.2 | (m, 3H) | —CH—OTHP, —CH—O— |
| | 5.4–5.6 | (m, 2H) | olefinic protons |
| | 6.8–7.25 | (m, 3H) | thiophen |

EXAMPLE 1 c

5-Iodo-16,16-dimethyl-18-oxa-11,15-bis-tetrahydropyranyloxy-PGI$_1$ methyl ester Obtained from 5-iodo-16,16-dimethyl-18-oxa-PGI$_1$ methyl ester, by reaction analogous to Example 1 a.

| NMR (CDCl$_3$) δ values: | 0.9 | (d, 6H) | —C(CH$_3$)$_2$ |
|---|---|---|---|
| | 1.1 | (t, 3H) | CH$_3$ |
| | 1.2–2.7 | (m, 24H) | —CH$_2$—, —CH< |
| | 3.2 | (s, 2H) | —OCH$_2$—C(CH$_3$)$_2$ |
| | 3.4 | (q, 2H) | —OCH$_2$—CH$_3$ |
| | 3.6 | (s, 3H) | OCH$_3$ |
| | 3.1–4.1 | (m, 6H) | —CH$_2$—O—, —CHO— |
| | 4.3–4.7 | (m, 3H) | CH—I, —O—CH—O— |
| | 5.3–5.6 | (m, 2H) | olefinic protons |

EXAMPLE 1 d

5-Iodo-16,16-dimethyl-18-oxa-11,15-bis-tetrahydropyranyloxy-20-nor-PGI$_1$ methyl ester Obtained from 5-iodo-16,16-dimethyl-18-oxa-20-nor-PGI$_1$ methyl ester, by reaction analogous to Example 1 a.

| NMR (CDCl$_3$) δ values: | 0.9 | (d, 6H) | —C(CH$_3$)$_2$ |
|---|---|---|---|
| | 1.1–2.6 | (m, 24H) | —CH$_2$—, >CH— |
| | 3.25 | (s, 3H) | —OCH$_3$ |
| | 3.6 | (s, 3H) | —COOCH$_3$ |
| | 3.1–4.1 | (m, 10H) | —OCH$_2$—, —OCH— |
| | 4.2–4.7 | (m, 3H) | —O—CH—O—, —CH—I |
| | 5.3–5.6 | (m, 2H) | olefinic protons |

EXAMPLE 1 e

5-Iodo-16,16-dimethyl-18-oxa-11,15-bis-tetrahydropyranyloxy-20-homo-PGI$_1$ methyl ester Obtained from 5-iodo-16,16-dimethyl-18-oxa-20-homo-PGI$_1$ methyl ester, by reaction analogous to Example 1 a.

| NMR (CDCl$_3$) δ values: | 0.9 | (d + t, 9H) | —C(CH$_3$)$_2$, —CH$_2$CH$_2$—CH$_3$ |
|---|---|---|---|
| | 1.1–2.6 | (m, 24H) | —CH$_2$—, >CH— |
| | 3.6 | (s, 3H) | —OCH$_3$ |
| | 3.0–4.1 | (m, 12H) | —OCH$_2$, —OCH— |
| | 4.2–4.7 | (m, 3H) | —O—CH—O—, —CH—I |
| | 5.3–5.6 | (m, 2H) | olefinic protons |

EXAMPLE 1 f

5-Iodo-16,16-dimethyl-11,15-bis-tetrahydropyranyloxy-PGI$_1$ methyl ester

Obtained from 5-iodo-16,16-dimethyl-PGI$_1$ methyl ester, by reaction analogous to Example 1 a.

| NMR (CDCl$_3$) δ values: | 0.9 | (t + d, 9H) | —C(CH$_3$)$_2$, CH$_3$— |
|---|---|---|---|
| | 1.0–2.6 | (m, 30H) | —CH$_2$—, >CH— |
| | 3.6 | (s, 3H) | —OCH$_3$ |
| | 3.2–4.2 | (m, 7H) | —CH$_2$O—, —CHO— |
| | 4.2–4.7 | (m, 3H) | —O—CH—O—, —CH—I |
| | 5.3–5.6 | (m, 2H) | olefinic protons |

EXAMPLE 1 g

5-Iodo-16-fluoro-11,15-bis-tetrahydropyranyloxy-PGI$_1$ methyl ester

Obtained from 5-iodo-16-fluoro-PGI$_1$ methyl ester, by reaction analogous to Example 1 a.

| NMR (CDCl$_3$) δ values: | 3.6 | (s, 3H) | —COOCH$_3$ |
|---|---|---|---|
| | 5.35–5.65 | (m, 2H) | olefinic protons |

EXAMPLE 1 h

5-Iodo-17-phenoxy-11,15-bis-tetrahydropyranyloxy-18,19,20-trinor-PGI$_1$ methyl ester Obtained from 5-iodo-17-phenoxy-18,19,20-trinor-PGI$_1$ methyl ester by reaction analogous to Example 1 a.

| NMR (CDCl$_3$): δ values: | 3.6 | (s, 3H) | COOCH$_3$ |
|---|---|---|---|
| | 5.3–5.6 | (m, 2H) | olefinic protons |
| | 6.8–7.3 | (m, 5H) | aromatic protons |

EXAMPLE 1 i

5-Iodo-16,16-dimethyl-16-(cyclohexyloxy)-11,15-bis-tetrahydropyranyloxy-17,18,19,20-tetranor-PGI$_1$ methyl ester Obtained from 5-iodo-16,16-dimethyl-16-(cyclohexyloxy)-17,18,19,20-tetranor-PGI$_1$ methyl ester by reaction analogous to Example 1 a.

| NMR (CDCl$_3$) δ values: | 1.0 | (d, 6H) | C(CH$_3$)$_2$ |
|---|---|---|---|
| | 0.9–3.0 | (m, 33H) | CH$_2$, >CH— |
| | 3.6 | (s, 3H) | —COCH$_3$ |
| | 5.3–5.6 | (m, 2H) | olefinic protons |

EXAMPLE 1 j

5-Iodo-15-cyclohexyl-11,15-bis-tetrahydropyranyloxy-16,17,18,19,20-pentanor-PGI$_1$ methyl ester Obtained from 5-iodo-15-cyclohexyl-16,17,18,19,20-pentanor-PGI$_1$ methyl ester by reaction analogous to Example 1 a.

| NMR (CDCl$_3$) δ values | 3.6 | (s, 3H) | —COOCH$_3$ |
|---|---|---|---|
| | 5.3–5.5 | (m, 2H) | olefinic protons |

EXAMPLE 2

16-(3-Thienyloxy)-11,15-bis-tetrahydropyranyloxy-17,18,19,20-tetranor-PGI$_2$ methyl ester III 0.57 g (1 mmole) of 5-iodo-16-(3-thienyloxy)-11,15-bis-tetrahydropyranyloxy-17,18,19,20-tetranor-PGI$_1$ methyl ester (Example 1a) are dissolved in 4.0 ml of 1,5-diazabicyclo[5.4.0]undec-5-ene with vigorous stirring. The solution is warmed at 70°–75° C. for about 1.5 hours. After the reaction has ended, the reaction mixture is taken up in 50 ml of ethyl acetate +30 ml of water. The organic phase is separated off and dried over MgSO$_4$, the mixture is filtered and the solvent is removed from the filtrate in vacuo; a pale yellow oil is obtained as the residue and this can be used further without further purification.

Yield: 0.49 g of (III).

| TLC in ethyl acetate/AcOH R$_f$ = 0.93 | |
|---|---|
| 97.5 | 2.5 |

Staining with molybdophosphoric acid, plates warmed to 100° C.

EXAMPLE 2 b to 2 j

Analogously to Example 2 a, compounds 2 b to 2 j (formula III), R$^1$=CH$_3$, can be prepared from the compounds of Examples 1 b to 1j, by the elimination of HI.

(Example 2 a) are dissolved in 30 ml of ethyl acetate and 8 ml of 2 N aqueous hydrochloric acid are added and the resulting mixture is stirred at room temperature for about 15 minutes. The organic phase is again separated off, dried over MgSO$_4$, filtered and concentrated in vacuo.

Yield: 0.47 g of a pale oil IV.

| TLC ethyl acetate/AcOH R$_f$ = 0.78 | | (molybdophosphoric acid, |
|---|---|---|
| 97.5 | 2.5 | plate warmed to 100° C.) |

NMR: δ values
in CDCl$_3$

| | | |
|---|---|---|
| 1.1–2.7 | (m, 26H) | —CH$_2$—, >CH— |
| 3.6 | (s, 3H) | OCH$_3$ |
| 3.1–4.1 | (m, 12H) | —CH—O—THP, —CH$_2$—O—, —OH |
| 4.3–4.9 | (m, 2H) | —O—CH—O— |
| 5.3–5.9 | (m, 2H) | olefinic protons |
| 6.1–7.3 | (m, 3H) | thiophen |

| Example 2 | R$^2$ | R$f$ values glacial acetic acid/ ethyl acetate = 2.5/97.5 |
|---|---|---|
| (a) | 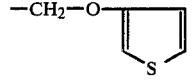 | 0.93 |
| (b) | 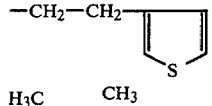 | 0.87 |
| (c) | 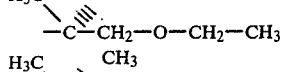 | (cyclohexane 2) 0.63 (ethyl acetate 1) |
| (d) | 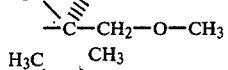 | 0.95 |
| (e) | 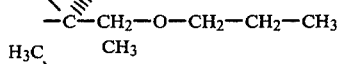 | 0.91 |
| (f) | 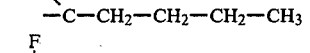 | 0.94 |
| (g) | 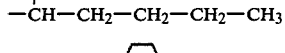 | |
| (h) | 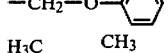 | |
| (i) | 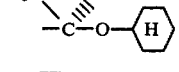 | |
| (j) |  | |

EXAMPLE 3 a

6-Keto-11,15-bis-tetrahydropyranyloxy-16-(3-thienyloxy)-17,18,19,20-tetranor-PGF$_1$ methyl ester IV 0.49 g of 16-(3-thienyloxy)-11,15-bis-tetrahydropyranyloxy-17,18,19,20-tetranor-PGI$_2$ methyl ester

EXAMPLE 3 b to 3j

Analogously to Example 3 a, compounds 3 b to 3j (formula IV), R$^1$=CH$_3$, can be prepared from the compounds of Examples 2 b to 2j by treatment with 2 N hydrochloric acid.

| Example 3 | R$^2$ | R$f$ values (glacial acetic acid/ ethyl acetate = 2.5/97.5) |
|---|---|---|
| (a) | 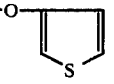 | 0.78 |

| Example 3 | R² | Rf values (glacial acetic acid/ ethyl acetate = 2.5/97.5) |
|---|---|---|
| (b) | —CH₂—CH₂—[2-thienyl]  | 0.73 |
| (c) | 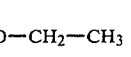 H₃C, CH₃ on —C—CH₂—O—CH₂—CH₃ (with triple bond between CH₃ groups indicated) | (cyclohexane 2) 0.15 (ethyl acetate 1) |
| (d) | 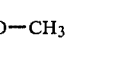 —C(CH₃)(C≡CCH₃)—CH₂—O—CH₃ | 0.80 |
| (e) | 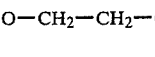 —C(CH₃)(C≡CCH₃)—CH₂—O—CH₂—CH₂—CH₃ | 0.85 |
| (f) | 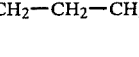 —C(CH₃)(C≡CCH₃)—CH₂—CH₂—CH₂—CH₃ | 0.83 |
| (g) | —CHF—CH₂—CH₂—CH₂—CH₃ | |
| (h) | —CH₂—O—C₆H₅ 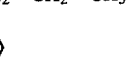 | |
| (i) |  —C(CH₃)(C≡CCH₃)—O—C₆H₅ | |
| (j) | —C₆H₅  | |

EXAMPLE 4 a

6-Keto-11,15-bis-tetrahydropyranyloxy-16-(3-thienyloxy)-17,18,19,20-tetranor-PGE₁ methyl ester V 0.4 g (0.7 mmole) of 6-keto-11,15-bis-tetrahydropyranyloxy-16-(3-thienyloxy)-17,18,19,20-tetranor-PGF₁ methyl ester (Example 3 a) is dissolved in 5 ml of acetone. 0.6 ml of "Jones" reagent (prepared from 1.05 g of chromium trioxide, 0.84 ml of sulfuric acid and 2 ml of water) is added dropwise at −20° to −25° C. After ½ an hour the reaction has ended and 1 ml of isopropanol is allowed to run in dropwise. (Color change from yellow-orange to green). 20 ml of NaCl solution and 50 ml of ethyl acetate are then added. After shaking, the ethyl acetate phase is washed with sodium bicarbonate until acid-free. The organic phase is dried over magnesium sulfate and concentrated in vacuo.

Yield: 0.38 g of a colorless oil.

TLC$_{in\ toluene/ethyl\ acetate,\ 1:1}$ R$_f$=0.38.

(Staining with molybdophosphoric acid, plate warmed to 100° C.).

EXAMPLE 4 b to 4j

Analogously to Example 4 a, compounds 4 b to 4 j (formula V), R¹=CH₃, can be prepared from the compounds of Examples 3 b to 3 j by oxidation with "Jones" reagent.

| Example 4 | R² | Rf values |
|---|---|---|
| (a) | —CH₂—O—[2-thienyl] 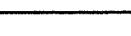 | (toluene 1) 0.38 (ethyl acetate 1) |
| (b) | —CH₂—CH₂—[2-thienyl] 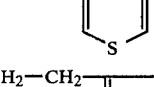 | (cyclohexane 2) 0.26 (ethyl acetate 1) |
| (c) | 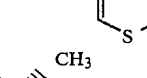 —C(CH₃)(C≡CCH₃)—CH₂—O—CH₂—CH₃ | (cyclohexane 1) 0.22 (ethyl acetate 1) |
| (d) | 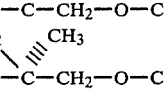 —C(CH₃)(C≡CCH₃)—CH₂—O—CH₃ | (cyclohexane 1) 0.19 (ethyl acetate 1) |
| (e) | 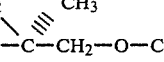 —C(CH₃)(C≡CCH₃)—CH₂—O—CH₂—CH₂—CH₃ | (cyclohexane 1) 0.25 (ethyl acetate 1) |
| (f) | 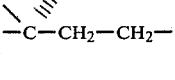 —C(CH₃)(C≡CCH₃)—CH₂—CH₂—CH₂—CH₃ | (cyclohexane 1) 0.23 (ethyl acetate 1) |
| (g) | —CHF—CH₂—CH₂—CH₂—CH₃ 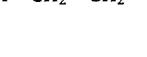 | |

-continued

| Example 4 | $R^2$ | $R_f$ values |
|---|---|---|
| (h) | $-CH_2-O-\phenyl$ | |
| (i) | $H_3C \diagdown \diagup CH_3$ $-C-O-\phenyl(H)$ | |
| (j) | $-\phenyl(H)$ | |

EXAMPLE 5 a

6-Keto-16-(3-thienyloxy)-17,18,19,20-tetranor-PGE$_1$ methyl ester I 280 mg (0.65 mmole) of 6-keto-11,15-bis-tetrahydropyranyloxy-16-(3-thienyloxy)-17,18,19,20-tetranor-PGE$_1$ methyl ester (Example 4a) are dissolved in 4 ml of THF. After adding 10 ml of 66% acetic acid, the reaction mixture is warmed at 50° C. for 2 hours, with stirring. 60 ml of ethyl acetate are then added to the reaction mixture, and 30 ml of saturated NaCl solution are added. After shaking, the organic layer is separated off and washed with saturated NaHCO$_3$ solution until acid-free. The aqueous phase is extracted twice more with ethyl acetate. The organic phases are combined, dried over MgSO$_4$, filtered and concentrated in vacuo.

Yield: 193 mg of a yellow oil.

The substance is purified on a Merck size B prepacked column (SiO$_2$-60). Eluant: 5/1 ethyl acetate/toluene.

Yield of pure product: 172 mg.

TLC$_{ethyl\ acetate}$ $R_f$=0.15.

| NMR δ values: | 1.0–2.95 | (m, 16H) | $-CH_2-$, $>CH-$, $-OH$ |
|---|---|---|---|
| in CDCl$_3$ | 3.6 | (s, 3H) | $-OCH_3$ |
| | 3.9 | (d, 2H) | $-CH_2O-$thiophen |
| | 4.1–4.6 | (m, 2H) | $-CH-OH$ |
| | 5.4–5.8 | (m, 2H) | olefinic protons |
| | 6.1–7.3 | (m, 3H) | thiophen |

EXAMPLE 5 b to 5j

Analogously to Example 5 a, compounds 5 b to 5 j (formula I), $R^1$=CH$_3$, can be prepared from the compounds of Examples 4 b to 4 j by detaching the protective groups $R^3$ using 66% strength acetic acid in THF.

| Example 5 | $R^2$ | δ values NMR (CDCl$_3$) |
|---|---|---|
| (a) | $-CH_2-O-\thiophene(S)$ | 1.0–2.95 (m, 16H) $-CH_2-$, $>CH-$, OH; 3.6 (s, 3H) $-OCH_3$; 3.9 (d, 2H) $-CH_2O-$thiophen; 4.1–4.6 (m, 2H) $-CH-OH$; 5.4–5.8 (m, 2H) olefinic protons, 6.1–7.3 (m, 3H) thiophen |
| (b) | $-CH_2-CH_2-\thiophene(S)$ | 0.95–3.0 (m, 20H) $-CH_2-$, $>CH$, OH; 3.6 (s,3H) $-OCH_3$; 3.7–4.5 (m, 2H) $-CH-OH$; 5.3–5.9 (m, 2H) olefinic protons 6.8–7.3 (m, 3H) thiophen |
| (c) | $H_3C \diagdown \diagup CH_3$ $-C-CH_2-O-CH_2-CH_3$ | 0.9 (s, 6H) C(CH$_3$)$_2$; 1.15 (t, 3H) $-CH_2CH_3$; 1.4–2.95 (m, 14H) $-CH_2-$ $>CH-$; 3.3 (s, 2H) $-OCH_2-$; 3.5 (q, 2H) $-OCH_2CH_3$; 3.6 (s, 3H) OCH$_3$; 3.8–4.5 (m, 2H) $-CH-OH$; 5.5–5.8 (m, 2H) olefinic protons |
| (d) | $H_3C \diagdown \diagup CH_3$ $-C-CH_2-O-CH_3$ | 0.9 (s, 6H) C(CH$_3$)$_2$; 1.1–2.9 (m, 16H) $-CH_2-$, $>CH$, OH; 3.2 (s, 2H) $-CH_2OCH_3$; 3.3 (s, 3H) $-CH_2-OCH_3$; 3.6 (s, 3H) $-COOCH_3$; 3.7–4.5 (m,2H) CHOH; 5.5–5.8 (m, 2H) olefinic protons |

-continued

| Example 5 | R² | δ values NMR (CDCl₃) |
|---|---|---|
| (e) | H₃C\\ ∭ CH₃<br>−C−CH₂−O−CH₂−CH₂−CH₃ | 0.9 (s + t, 9H) −C(CH₃)₂, CH₃; 1.2–2.9 (m, 16H) −CH₂−, >CH−; 3.25 (s, 2H) −CH₂O−; 3.35 (t, 2H) −O−CH₂CH₂CH₃; 3.6 (s, 3H) −COOCH₃; 3.7–4.4 (m, 2H) −CH−OH; 5.5–5.7 (m, 2H) olefinic protons |
| (f) | H₃C\\ ∭ CH₃<br>−C−CH₂−CH₂−CH₂−CH₃ | 0.9 (s + t, 9H) −(CH₃), CH₃; 3.6 (s, 3H) −COOCH₃ 5.5–5.7 (m, 2H) olefinic protons |
| (g) | F<br>\|<br>−CH−CH₂−CH₂−CH₂−CH₃ | 0.95 (t, 3H) CH₃, 3.6 (s, 3H)−COOCH₃ 5.45–5.6 (m, 2H) olefinic protons |
| (h) | −CH₂−O−⟨Ph⟩ | 3.85 (d, 2H) −CH₂−O−Ph 3.6 (s, 3H) −COOCH₃ 5.5–5.7 (m, 2H) olefinic protons 6.8–7.3 (m, 5H) aromatic protons |
| (i) | H₃C\\ ∭ CH₃<br>−C−O−⟨H⟩ | 1.05 (d, 6H) C<(CH₃)₂; 0.9–3.1 (m, 23H) −CH₂, CH−, OH; 3.6 (s, 3H) OCH₃; 3.4–4.3 (m, 3H) CH−OH, −CH−O−; 5.5–5.75 (m, 2H) olefinic protons |
| (j) | −⟨H⟩ | 1.0–3.0 (m, 26H) −CH₂−, CH, OH, 3.6 (s, 3H) −COOCH₃, 5.45–5.65 (m, 2H) olefinic protons |

EXAMPLE 6 a

6-Keto-16-(3-thienyloxy)-17,18,19,20-tetranor-PGE₁ I 170 mg (0.4 mmole) of 6-keto-16-(3-thienyloxy)-17,18,19,20-tetranor-PGE₁ methyl ester (Example 5 *a*) are dissolved in 30 ml of 80% ethanol. A solution of 67.5 mg of sodium in 4 ml of ethanol is added to this solution, with stirring. The resulting mixture is stirred for 3 hours at 35° under argon and acidified to pH 4 with 2 N citric acid solution, with ice-cooling, and the reaction mixture is extracted with ethyl acetate, the organic phase is dried over MgSO₄ and filtered and the solvent is removed in vacuo.

Yield: 150 mg of a brown oil.

Column chromatography on a Merck size A prepacked column (SiO₂-60) with ethyl acetate gives 95 mg of a colorless oil.

| NMR: | 1.0–2.9 | (m, 15H) | −CH₂, >CH−, |
|---|---|---|---|
| | 3.9 | (d, 2H) | −CH₂O−thiophen |
| | 4.1–4.8 | (m, 2H) | −CH−OH |
| | 4.9–5.2 | (broad s, 3H) | OH, COOH |
| | 5.4–5.8 | (m, 2H) | olefinic protons |
| | 6.1–7.3 | (m, 3H) | thiophen |

EXAMPLE 6 b to 6j

Analogously to Example 6 *a*, compounds 6 *b* to 6 *j* (formula I), R¹=H, can be prepared from the compounds 5 *b* to 5 *j* by ester saponification.

| Example 6 | R² |
|---|---|
| (a) | −CH₂−O−⟨thiophen-S⟩ |
| (b) | −CH₂−CH₂−⟨thiophen-S⟩ |
| (c) | H₃C\\ ∭ CH₃<br>−C−CH₂−O−CH₂−CH₃ |
| (d) | H₃C\\ ∭ CH₃<br>−C−CH₂−O−CH₃ |
| (e) | H₃C\\ CH₃<br>−C−CH₂−O−CH₂−CH₂−CH₃ |
| (f) | H₃C\\ CH₃<br>−C−CH₂−CH₂−CH₂−CH₃ |
| (g) | F<br>\|<br>−CH−CH₂−CH₂−CH₂−CH₃ |
| (h) | −CH₂−O−⟨Ph⟩ |
| (i) | H₃C\\ CH₃<br>−C−C−O−⟨H⟩ |
| (j) | −⟨H⟩ |

EXAMPLE 7 a

The sodium salt of 6-keto-16-(3-thienyloxy)-17,18,19,20-tetranor-PGE₁ I 170 mg (0.4 mmole) of 6-keto-16-(3-thienyloxy)-17,18,19,20-tetranor-PGE₁ methyl ester (Example 5 *a* ) are dissolved in 30 ml of 80% ethanol. A solution of 67 mg of sodium in 4 ml of ethanol is added to this solution, with stirring. The resulting mixture is stirred for 3 hours at 35° C. under argon, the solution is filtered through active charcoal and the solvent is removed in vacuo at −10° C. (freeze drying). The sodium salt of the prostaglandin derivative is obtained in the form of a colorless powder.

EXAMPLE 7 b

The potassium salt of 6-keto-16-(3-thienyloxy)-17,18,19,20-tetranor-PGE₁ I 192 mg of pure 6-keto-16-(3-thienyloxy)-17,18,19,20-tetranor-PGE₁ methyl ester (Example 5 a), 1.1 ml of 0.5 M potassium hydroxide solution and 2 ml of methanol are allowed to stand at room temperature for 24 hours under an inert gas. The methanol is stripped off in vacuo and the aqueous solution of the potassium salt is freeze-dried. The potassium salt of the prostaglandin derivative is obtained in the form of a colorless powder.

EXAMPLE 7 c

Triethylammonium salt of 6-keto-16-(3-thienyloxy)-17,18,19,20-tetranor-PGE₁ I

An aqueous solution of 50 mg of the sodium salt of 6-keto-16-(3-thienyloxy)-17,18,19,20-tetranor-PGE₁ (Example 7 a) is introduced into a column containing 15 g of Amberlite CG - 50 (triethylammonium form). The product is eluted with a 3% strength aqueous solution of triethylammonium carbonate. On freeze-drying the eluate, the product is obtained in the form of a crystalline powder (decomposition >50° C.).

EXAMPLE 7 d

Analogously to Example 7 a to 7 c, the corresponding alkali metal salts or ammonium salts of the compounds of Examples 6 a to 6 j can be prepared from the said compounds by alkaline ester saponification and, if necessary, chromatography on ion exchangers.

What is claimed is:
1. A compound of the formula

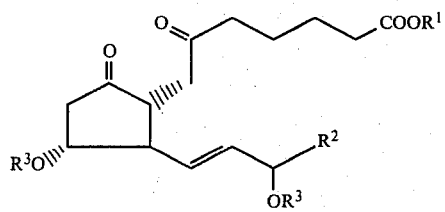

wherein
$R^1$ is hydrogen, linear or branched alkyl having up to 8 carbon atoms, linear or branched unsaturated aliphatic hydrocarbon having 3 to 6 carbon atoms, cycloaliphatic hydrocarbon having 3 to 7 carbon atoms, araliphatic hydrocarbon having 7 to 9 carbon atoms, a physiologically acceptable metal ion, $NH_4^+$ ion, an ammonium ion derived from a primary, secondary or tertiary amine or a tetraalkylammonium ion;
$R^2$ is linear or branched alkyl having up to 8 carbon atoms and substituted with α- or β-thienyl, α- or β-thienyloxy, α- or β-furyl, or such thienyl, thienyloxy, or furyl mono-, di-, or tri-substituted in the nucleus with halogen, trifluoromethyl, or alkyl or alkoxy each having 1 to 6 carbon atoms; and
$R^3$ is hydrogen or an easily-detachable protective group.

2. A compound as in claim 1 wherein $R^3$ is an easily-detachable protective group.

3. A compound as in claim 1 wherein $R^3$ is hydrogen.

4. A pharmaceutical preparation for the treatment of thromboses, infarcts, or hypertension, which preparations comprise an effective amount of a compound as in claim 3 and a pharmaceutically acceptable carrier therefor.

5. A method for treating thromboses, infarcts, or hypertension in a patient suffering from one or more of the same, which method comprises orally, parenterally, or locally administering to said patient an effective amount of a compound as in claim 3.

* * * * *